United States Patent [19]

Urion et al.

[11] Patent Number: 5,680,859

[45] Date of Patent: Oct. 28, 1997

[54] INTEGRATED INTRODUCER AND DRIVE ROD POSITIONING SYSTEM FOR A FETAL SPIRAL ELECTRODE

[75] Inventors: Kenard E. Urion, Woodbury, N.J.; George R. Allen, Grand Island, N.Y.; Richard A. Clement, Stratford; Clete A. Eichelberger, Delran, both of N.J.

[73] Assignee: Graphic Controls Corporation, Buffalo, N.Y.

[21] Appl. No.: 540,920

[22] Filed: Oct. 11, 1995

[51] Int. Cl.$^6$ ............................................. A61B 5/0448
[52] U.S. Cl. ............................................. 128/642
[58] Field of Search ............................ 128/642, 698; 607/127

[56] References Cited

U.S. PATENT DOCUMENTS

| | | |
|---|---|---|
| Re. 28,990 | 10/1976 | Hon et al. . |
| 4,254,773 | 3/1981 | Waldbillig . |
| 4,281,659 | 8/1981 | Farrar et al. . |
| 4,320,764 | 3/1982 | Hon . |
| 4,437,467 | 3/1984 | Helfer et al. ........................... 128/642 |
| 4,600,402 | 7/1986 | Rosenberg . |
| 4,624,266 | 11/1986 | Kane . |
| 4,628,943 | 12/1986 | Miller . |
| 4,644,957 | 2/1987 | Ricciardelli et al. . |
| 4,667,686 | 5/1987 | Peers-Travarton . |
| 4,836,208 | 6/1989 | Ulbrich . |
| 4,852,564 | 8/1989 | Sheridan et al. . |
| 4,913,151 | 4/1990 | Harui et al. ........................... 128/642 |
| 5,012,811 | 5/1991 | Malis et al. . |
| 5,074,846 | 12/1991 | Clegg et al. . |
| 5,199,432 | 4/1993 | Quedens et al. . |
| 5,222,498 | 6/1993 | Neward . |
| 5,243,995 | 9/1993 | Maier . |
| 5,247,942 | 9/1993 | Prather et al. . |
| 5,312,352 | 5/1994 | Leschinsky et al. . |
| 5,377,677 | 1/1995 | Dowd et al. . |
| 5,388,579 | 2/1995 | Dowd et al. . |
| 5,423,314 | 6/1995 | Schmid . |

FOREIGN PATENT DOCUMENTS

1457426  12/1976  United Kingdom ................... 128/642

*Primary Examiner*—Lee S. Cohen
*Attorney, Agent, or Firm*—Ratner & Prestia

[57] ABSTRACT

An integrated introducer and drive rod system used to position and attach a spiral-shaped, biological needle probe to a fetus during labor and delivery. The system ensures that the sharp, pointed, probe (typically, a fetal spiral electrode) remains protected in a retracted position inside the introducer until attachment to the fetal scalp is desired. The flexible drive rod of the system has a "C"-shaped safety ring with an outside diameter slightly less than the inner diameter of the introducer at a point on the introducer; a "C"-shaped radial web with an outside diameter only slightly larger than the inner diameter of the introducer creating an interference fit between the drive rod and the introducer; or a "C"-shaped segmented rib that engages the rear end of the introducer. The introducer has an inner diameter sized to create an interference fit with the drive rod; a forward interior wall with an inside diameter slightly less than the outside diameter of the safety ring; a ramp on the front end of the introducer; a longitudinal slot disposed along its entire length; or a combination of one or more of these structures. In combination, the structures of the drive rod and introducer resist but (upon exertion of a predetermined force on the handle of the drive rod) allow translation of the drive rod within the introducer.

24 Claims, 6 Drawing Sheets

INTEGRATED INTRODUCER AND DRIVE ROD POSITIONING SYSTEM FOR A FETAL SPIRAL ELECTRODE

FIELD OF THE INVENTION

The present invention relates to applicators for attaching spiral-shaped, biological needle probes and, in particular, to an integrated introducer and drive rod system used to position and attach a fetal spiral electrode.

BACKGROUND OF THE INVENTION

It is desirable to monitor the biological functions (such as heart rate) of a fetus continuously during labor and delivery in order to detect fetal distress. Devices which are external to the mother's body are insufficiently sensitive. In the case of heart rate signals, they do not adequately isolate the fetal and maternal heartbeats. Consequently, devices which attach directly to the fetus during labor are used. U.S. Pat. No. Re. 28,990, issued to Hon et al., discloses a fetal spiral electrode assembly commonly used to monitor fetal heart rate during birth.

The conventional fetal spiral electrode assembly includes a curved guide tube of adjustable shape for insertion of the fetal spiral electrode through the mother's cervix and into contact with the fetus during labor. A plastic tip or holder is slidably received in the guide tube. A sharp, pointed, fetal spiral electrode is mounted on the forward end of the holder for contacting the fetal epidermis.

A reference (maternal) electrode in the form of a flat fin or plate is electrically isolated from the fetal electrode and located on the rear end of the holder. A flexible, hollow drive tube with a cutout on its forward end fits inside the guide tube and engages the holder. The cutout of the drive tube engages the reference electrode in the holder to impart translation and rotation to the holder and, hence, to the fetal spiral electrode. A handle on the opposite end of the drive tube allows the user to push, pull, and rotate the drive tube within the guide tube. A forward-twisting force is applied to the drive tube to affix the fetal-spiral electrode in the fetal epidermis.

The two electrodes are connected to separate wires which are threaded through the common center of the drive and guide tubes until they ultimately exit at the rear end of the drive tube. After the fetal spiral electrode is secured to the fetal epidermis, the drive tube and guide tube are removed by pulling the tubes longitudinally over the wires and away from the mother. Removal of the drive and guide tubes leaves the electrodes, the holder, and the wires in place inside the mother. The bare, uninsulated ends of the wires are then connected, via an intermediate support plate, to a fetal monitor.

To use the fetal spiral electrode product, the shape of the guide tube is adjusted and the guide tube is inserted through the mother's cervix and into contact with the fetus. Once the guide tube contacts the fetus (and is held against the fetus using one of the user's hands), the drive tube is advanced (using the second hand) until the fetal spiral electrode contacts the fetus. While pressure is maintained against the fetus by the guide tube and drive tube, the drive tube is rotated, using the second hand and the handle, until the fetal spiral electrode is secured to the fetal epidermis. Typically, one full revolution suffices to secure the fetal spiral electrode. Then the drive tube and guide tube are removed by sliding them over the electrode wires.

U.S. Pat. No. 5,388,579 issued to Dowd et al. is an improvement over the device disclosed in the '990 patent. Manual connection of the uninsulated ends of the wires is cumbersome and risks shorting the wires. If shorted, the wires cannot transmit correct signals from the fetal and reference electrodes. Accordingly, the '579 patent adds a connector to the wire ends of the fetal spiral electrode assembly disclosed in the '990 patent.

The connector solves the problem of manual connection of the uninsulated ends of the electrode wires. But the connector creates its own problem. The wires and the connector, which convey the electrical signal from the fetus to the monitor, must traverse through the hollow center of the drive tube. Because conventional guide and drive tubes are removed by pulling them longitudinally over the wires and connector, however, the connector must have an outer dimension which is smaller than the inside diameter of the drive tube and, of course, the larger-diameter guide tube as well. The guide and drive tubes must be small in diameter in order to transit the closed cervix. Consequently, the connector diameter must be relatively small.

The requirement of a small-diameter connector has several disadvantages. First, the clinician must grasp and handle the connector to insert it into the corresponding socket of the support plate. The smaller the connector, the more difficult it is to handle. Second, a proper connection of the connector to the support plate must be ensured. A smaller connector of constant cross-section is unable to provide assurance that the required connection has been achieved. Finally, the support plate and fetal spiral electrode operate in a fluid-filled environment. A smaller connector risks an inadequate seal of the opening in the support plate into which the connector is inserted. Absent an adequate seal, fluid from the environment may enter the opening in the support plate and adversely affect the connector-socket electrical connection or the other electrical circuit paths.

The '579 patent alleviates the problem of a small-diameter connector somewhat. The drive mechanism, which slides and rotates the holder to secure attachment of the fetal spiral electrode to the fetus, has (a) a solid drive rod with at least two regions of different diameter defining the torque versus angular deflection characteristics of the drive rod, (b) a handle connected to the drive rod and imparting translation and rotation to the drive rod, and (c) a clutch connected to the drive rod and imparting translation and rotation to the holder. The drive rod, handle, and clutch are integrally molded together to form the drive mechanism. Each of the drive rod, handle, and clutch has a channel transporting the twisted wire strand from the electrodes to the connector.

The device of the '579 patent includes an annular guide tube sized to be comfortably inserted through the cervix of a mother in labor. The connector has an outside dimension greater than the outside diameter of the drive rod to facilitate handling and smaller than the inside diameter of the annular guide tube so that the guide tube can be pulled over the connector after the fetal spiral electrode is attached to the fetus.

U.S. Pat. No. 4,644,957, issued to Ricciardelli et al., avoids the problem of a small-diameter connector entirely. The '957 patent avoids that problem by placing the wires alongside a solid drive wrench (rather than inside an annular drive tube) and by providing a slotted guide with a C-shaped cross-section (as opposed to a solid, annular guide tube). The wires reside freely inside the guide and parallel to the drive wrench. Because the wires are of a smaller diameter than the width of the longitudinal slot in the guide (enabling the wires to exit the slot), they must either be wound in a spiral around the drive wrench or positioned in the guide away from the slot to retain them securely inside the guide. After the fetal spiral electrode is secured to the fetus, the drive wrench is pulled out of the guide. The guide is then withdrawn, in a similar manner, as the wires slip freely out of the longitudinal slot in the guide.

The solution presented by the '957 patent has its own difficulties. The wires may exit the slot prematurely. More important, the wires reside freely inside the guide and may affect rotation of the drive wrench. The wires may become entangled around the drive wrench, in the worst case, preventing both rotation and removal of the drive wrench. The risk of entanglement is especially great if the wires are purposefully wound in a spiral around the drive wrench. Finally, the wires may not be aligned with the slot, after the drive wrench is removed, rendering withdrawal of the guide difficult.

Another drawback of the conventional fetal spiral electrode assembly described above is the potential for the fetal spiral electrode to extend out of the guide tube and to disengage the drive rod clutch, during storage or transportation, before the fetal spiral electrode assembly is ready for use. If exposed, the sharp fetal spiral electrode can pierce the package, typically a paper and plastic pouch, in which the assembly is stored and transported. A person handling the electrode (or the patient) may then be harmed and sterilization of the electrode is jeopardized. In addition, the electrode itself may be damaged.

A related problem associated with the fetal spiral electrode assembly described above is the potential for the fetal spiral electrode to extend out of the guide tube during the initial stages of insertion. Such premature extension may injure the patient and may cause infection. The problem of premature extension of the fetal spiral electrode out of the guide tube, before or during the initial stages of use, was addressed by the '957 patent.

The drive wrench, monitor interconnecting cable, and retaining coil of the '957 patent are held firmly in the guide at a predetermined distance from the forward end, i.e., in a slightly recessed position relative to the forward end of the guide. The drive wrench and retaining coil are prevented from moving forward by wedging the monitor interconnecting cable between the guide and a shoulder located on the rear end of the drive wrench. By rotating the drive wrench approximately a quarter-turn, the cable is released into the longitudinal slot of the guide so that the retaining coil can be advanced.

The solution presented by the '957 patent is not without difficulties. The wedging action of the monitor interconnecting cable does not effectively retain the drive wrench and retaining coil in place. During storage of the applicator, this problem is further exacerbated by the outward radial stresses exerted by the drive wrench upon the C-shaped longitudinal guide. These stresses cause the guide walls to relax such that the tension upon the guide and monitor interconnecting cable is reduced.

The problem of premature extension of the fetal spiral electrode out of the guide tube, before or during the initial stages of use, has been solved by the '579 patent. A flexible safety clip is integrally mounted at a shoulder on the handle of the drive mechanism to protect the fetal spiral electrode in a recessed position inside the guide tube. The tail of the clip is adapted to be wedged snugly between the inner diameter of the guide tube and the outer diameter of the drive mechanism during storage and handling before and during the initial stages of use.

The clip has a body which is wider than its tail. The body is too wide to fit inside the guide tube. The shoulder on the body limits the distance by which the clip extends into the guide tube. Thus, the clip maintains a predetermined distance between the shoulder of the handle and the guide tube during storage and initial use. The total length of the clip (about 13 mm or 0.5 inches) and the length of the tail (about 5 mm or 0.2 inches) assure that the handle is not mounted completely inside the guide tube when the clip is wedged in position.

By maintaining this predetermined distance, the drive rod is retracted far enough inside the guide tube so that the holder and the fetal spiral electrode are retained in a protected position inside the guide tube. Because the clip is wedged between the drive rod and the guide tube, relative motion between the two is effectively prevented and the drive rod cannot slip out of the guide tube accidentally during handling.

The packaging system for a fetal electrode disclosed in U.S. Pat. No. 5,377,677 issued to Dowd et al. also addresses the problem of premature extension of the fetal spiral electrode out of the guide tube. The packaging system includes a clip with a head mounted (either detachably or integrally) to the handle of the fetal spiral electrode assembly. The clip has a tail which can be wedged between the rearward end of the guide tube and the rearward end of the drive tube when the handle is not mounted inside the guide tube. The holder and the fetal spiral electrode are retracted in (and protected by) the guide tube when the handle is secured by the clip.

Unlike the detachable clip, the integral embodiment of the clip need not be removed from the electrode assembly in order to use the fetal spiral electrode assembly. Rather, the guide tube is simply pulled away from the handle (and, therefore, the drive tube) a slight distance of about 0.4 inches (1 cm) while holding the handle. That action will remove the tail from between the drive tube and the guide tube, once the guide tube is pulled beyond the end of the tail of the clip, and the tail will spring open. The clip is preferably molded from a flexible plastic material and, accordingly, has an inherent bias returning the clip to its initial (as molded) "open" position.

Thus, the clinician can release the integral clip without directly contacting the clip—no additional hands are required to release the clip. This feature of the integral clip is advantageous because, at the point during use when the fetal spiral electrode will be affixed to the fetal epidermis, the clinician is grasping the handle with one hand and the guide tube with the other hand. Moreover, unlike the detachable clip, the integral clip need not be removed from the electrode assembly or discarded.

One disadvantage of either the integral or detachable safety clips is that they require an additional procedural step during use. The guide tube must be pulled away from the handle a slight distance to remove the tail of the clip from between the drive tube and the guide tube. Given the adverse environment and the time constraints that exist during use, clinicians desire as few procedural steps as possible.

U.S. Pat. No. 4,836,208 issued to Ulbrich discloses an electrode assembly for sensing fetal heart activity during delivery. The introducer includes a rigid drive tube that engages the holder for the fetal spiral electrode. The drive tube is rotated by a handle and is hollow to allow a pair of electrode wires to pass through its center. The electrode wires are connected to the fetal spiral electrode and to the reference electrode. A sleeve (akin to the guide tube of the systems discussed above) covers the fetal spiral electrode. The sleeve slides over the drive tube in an axial direction to protect or expose the fetal spiral electrode.

The sleeve also serves as a fixed bearing: the clinician grasps the sleeve while rotating the handle to affix the fetal electrode to the fetal tissue. Two guide rings on the drive tube facilitate rotation of the sleeve after it is retracted to expose the fetal electrode. To hinder movement of the sleeve in the axial direction during insertion, a set of detent rings is provided on the drive tube. A pawl, formed as a cut-out section of the sleeve with an enlarged tip, rides in the grooves created by the detent rings. An additional ring stops the forward axial movement of the sleeve on the drive tube so that the sleeve does not accidentally fall off.

In operation, the clinician introduces the assembly into the birth canal until the end of the sleeve presses against the fetal epidermis. Upon the continued application of an axial force on the drive tube handle, the sleeve retracts. When the last detent ring of the group of rings passes the pawl tip, the clinician senses the freedom of movement and rotates the drive handle to engage the electrode in the epidermis of the fetus.

Although it has a cut out pawl section, the sleeve is a complete, integral "tube" without any longitudinal slot. Thus, the sleeve must have an inside diameter large enough to permit the detent rings and safety rings located on the drive tube to pass along the longitudinal axis within the sleeve. Moreover, the electrode wires pass inside the hollow drive tube and sleeve. The size of any connector attached to the end of the wires, therefore, is inherently limited.

The pawl mechanism of the '208 patent also has the drawback that it only exerts a radially inward force at the point of contact between the enlarged tip of the pawl and the detent rings and not around the circumference of the rings. Only the enlarged tip of the pawl, and not the entire inside surface of the sleeve, applies a radially inward force to the detent rings. As a result, the force necessary to overcome the resistance between the pawl and the detent rings cannot be readily controlled. Finally, the user must force the pawl past multiple detent rings—an unnecessarily restrictive safety mechanism wasteful of time and energy.

In an alternative embodiment of the sleeve of the '208 patent, the sleeve has a round protrusion extending from its interior surface. The protrusion slides within a complex, circumferential-and-longitudinal groove system on the drive tube. The protrusion slides from a first, locked position in the circumferential groove to a second, freely rotatable position at the opened end of the longitudinal groove.

U.S. Pat. No. 5,012,811 issued to Malis et al. discloses a fetal electrode device with a protective cap designed to sheath the fetal spiral electrode during both application and removal of the electrode. The device includes a conventional guide tube having an open end through which a holder member slides. The holder member mounts the fetal spiral electrode in its forward end and a flat maternal electrode in its rear end. A conventional drive tube slides and rotates within the guide tube for positioning and rotating the holder to screw the fetal spiral electrode into the fetal epidermis.

The protective cap is mounted on the holder member. In a first embodiment, the holder member has a helical groove. The groove mates with a complementary helical rib on the interior surface of the cap to maintain the cap in position. A retaining ring extends circumferentially around the holder member toward the rear thereof. The ring protrudes slightly to function as a stop or retainer abutting against the top of the cap to limit its rearward movement on the holder member when the rib and groove are disengaged.

In a second embodiment, ridges on the cap engage grooves on the holder member. The holder member is attached to the cap via the ridges and grooves and relative axial movement between the holder and cap is prohibited. Thus, the ridges do not slide over the grooves. Contrast the permitted axial movement between the cap and holder member in the first embodiment.

Although both embodiments of the '811 patent function to protect the fetal spiral electrode, a protective cap performs that function in both cases. The cap has the drawback that it is cumbersome to use and, more important, involves an additional mechanical part which can fail during insertion and removal of the fetal spiral electrode. The '811 patent does not suggest modification to either the drive tube or guide tube of conventional fetal spiral electrode systems.

To overcome the shortcomings of conventional fetal spiral electrode systems, an integrated introducer and drive rod system used to position and attach a fetal spiral electrode is provided. The principal object of the present invention is to provide an improved system that protects the fetal spiral electrode in a retracted position inside the introducer until attachment to the fetal scalp is desired. Another object is to provide an integrated system in that it is used with the components (e.g., fetal spiral electrode, holder, connecting wires, and connector) of conventional electrode systems. A related object is to avoid separate, added components; the system is integral with existing components.

Another object of the present invention is to provide a system in which movement between the introducer and drive rod is restrained, but not prohibited, by a radial force exerted against the introducer by the drive rod around substantially the entire circumference of the introducer. Yet another object is to provide a system whose components are designed so that a controlled, predetermined axial force on the drive rod overcomes the radial force and permits movement of the drive rod relative to the introducer.

It is still another object of the present invention to provide a system that is easy to use; it only requires one hand to manipulate and can be operated without regard to directionality. An additional object is to reduce the number of procedural steps required to use the system. Yet another object of this invention is to ease manufacture of the system. A related object is to provide a system whose components permit the use of production methods, such as injection molding, which offer advantages over the extrusion methods used to produce prior art components.

SUMMARY OF THE INVENTION

To achieve these and other objects, and in view of its purposes, the present invention provides an integrated introducer and drive rod system used to position and attach a spiral-shaped, biological needle probe to a fetus during labor and delivery. The system ensures that the sharp, pointed, fetal probe (typically, a fetal spiral electrode) remains protected in a retracted position inside the introducer until attachment to the fetal scalp is desired. The probe is affixed to one end of a holder having a maternal reference electrode in its opposite end. A twisted wire strand includes a pair of wires respectively connecting the probe and the maternal reference electrode to a monitor external to the mother.

The solid drive rod of the integrated introducer and drive rod system has a handle on its rearward end imparting translation and rotation to the drive rod. A clutch on the forward end imparts translation and rotation to the holder to secure attachment of the probe to the fetus. A channel longitudinally disposed in the drive rod transports the twisted wire strand from the probe and the maternal reference electrode to the monitor. Finally, the drive rod has structure, disposed around its circumference, that resists and, upon exertion of a predetermined force on the handle, allows translation of said drive rod within the introducer.

In one embodiment of the system of the present invention, the drive rod structure is a "C"-shaped safety ring with an outside diameter slightly greater than the inner diameter of the introducer at a point on the introducer. The drive rod structure is a "C"-shaped radial web, having an outside diameter only slightly larger than the inner diameter of the introducer creating an interference fit between the drive rod and the introducer, in another embodiment. Finally, the drive rod structure may be a "C"-shaped segmented rib that engages the rear end of the introducer.

The introducer of the integrated introducer and drive rod system of the present invention has an outer diameter only slightly greater than the outside diameter of the drive rod; such an outer diameter allows the introducer to be comfortably inserted through the cervix of the mother. The introducer has structure disposed around its inner diameter that resists and, upon exertion of the predetermined force on the handle of the drive rod, allows translation of the drive rod within the introducer. This structure may be an inner diameter sized to create an interference fit with the drive rod; a forward interior wall having an inside diameter slightly less than the outside diameter of the safety ring; a ramp on the front end of the introducer; a longitudinal slot disposed along its entire length having a width sufficient to permit passage of the twisted wire strand and expansion of the introducer upon exertion of the predetermined force on the handle of the drive rod, thereby allowing translation of the drive rod; or a combination of one or more of these structures.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing, in which.

DETAILED DESCRIPTION OF THE INVENTION

Figure 1:
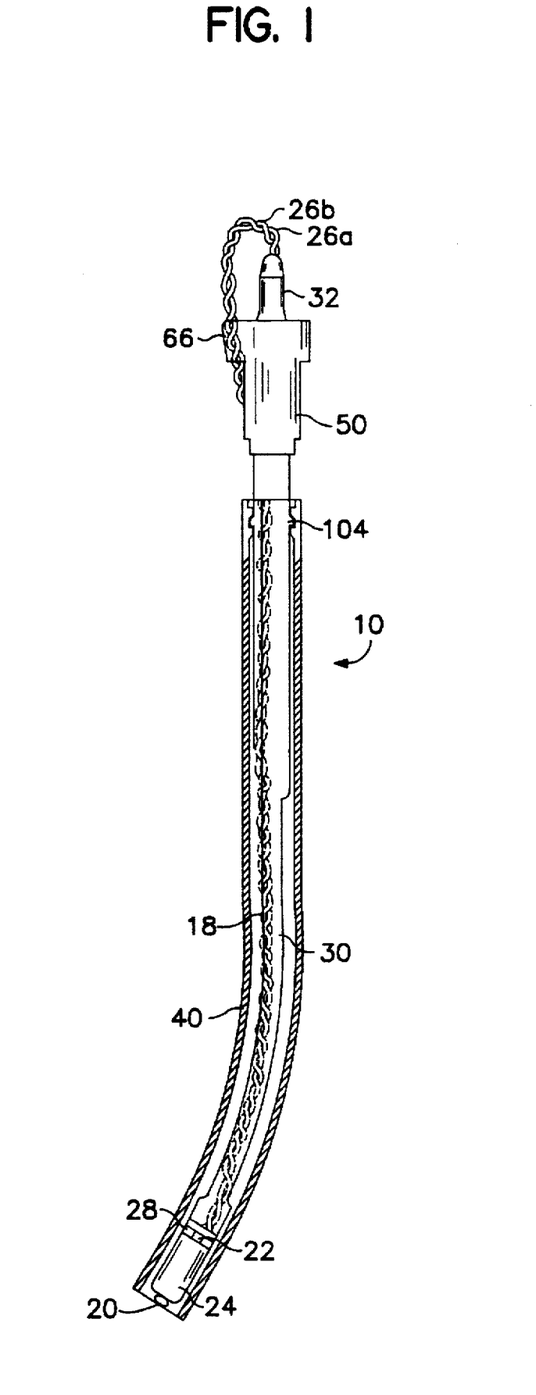
FIG. 1 is a side view of an exemplary fetal spiral electrode system in accordance with the present invention.

Referring now to the drawing, wherein like reference numerals refer to like elements throughout, FIG. 1 is a side view of an exemplary fetal spiral electrode system 10 in accordance with the present invention. It is emphasized that the various components shown in the drawing are not to scale. On the contrary, the dimensions of the various components are arbitrarily expanded or reduced for clarity. Electrode system 10 includes a sharp, pointed fetal spiral electrode 20 for contacting the fetal epidermis; a reference (maternal) electrode 22 in the form of a flat fin or plate which is electrically isolated from fetal spiral electrode 20; a holder 24; and two electrode wires 26a and 26b.

Holder 24 is an electrically insulating plastic and is adapted to be slidably received inside an introducer 40. Introducer 40 is discussed in greater detail below. Fetal spiral electrode 20 is mounted on the forward end of holder 24. Reference electrode 22 is attached to the rearward end of holder 24.

A drive rod 30 is slidably received in introducer 40. Drive rod 30 has a clutch 28 at its forward end. Clutch 28 engages reference electrode 22 in holder 24 to impart translation and rotation to holder 24 and, hence, to fetal spiral electrode 20. A handle 50 on the opposite end of drive rod 30 allows the user to push, pull, and rotate drive rod 30. Drive rod 30, clutch 28, and handle 50 are integrally molded together.

Electrode wires 26a and 26b are separately coupled to respective electrodes 20 and 22. Electrode wire 26a (typically green in color) connected to fetal spiral electrode 20 and electrode wire 26b (typically red) connected to reference electrode 22 form a twisted wire strand 18 which extends from electrodes 20 and 22 along the entire length of drive rod 30 and handle 50. A retainer 66 is provided near the end of handle 50 opposite drive rod 30. Retainer 66 locks wire strand 18 in a fixed position. The ends of wires 26a and 26b opposite holder 24 terminate in a male connector 32.

Figure 2:
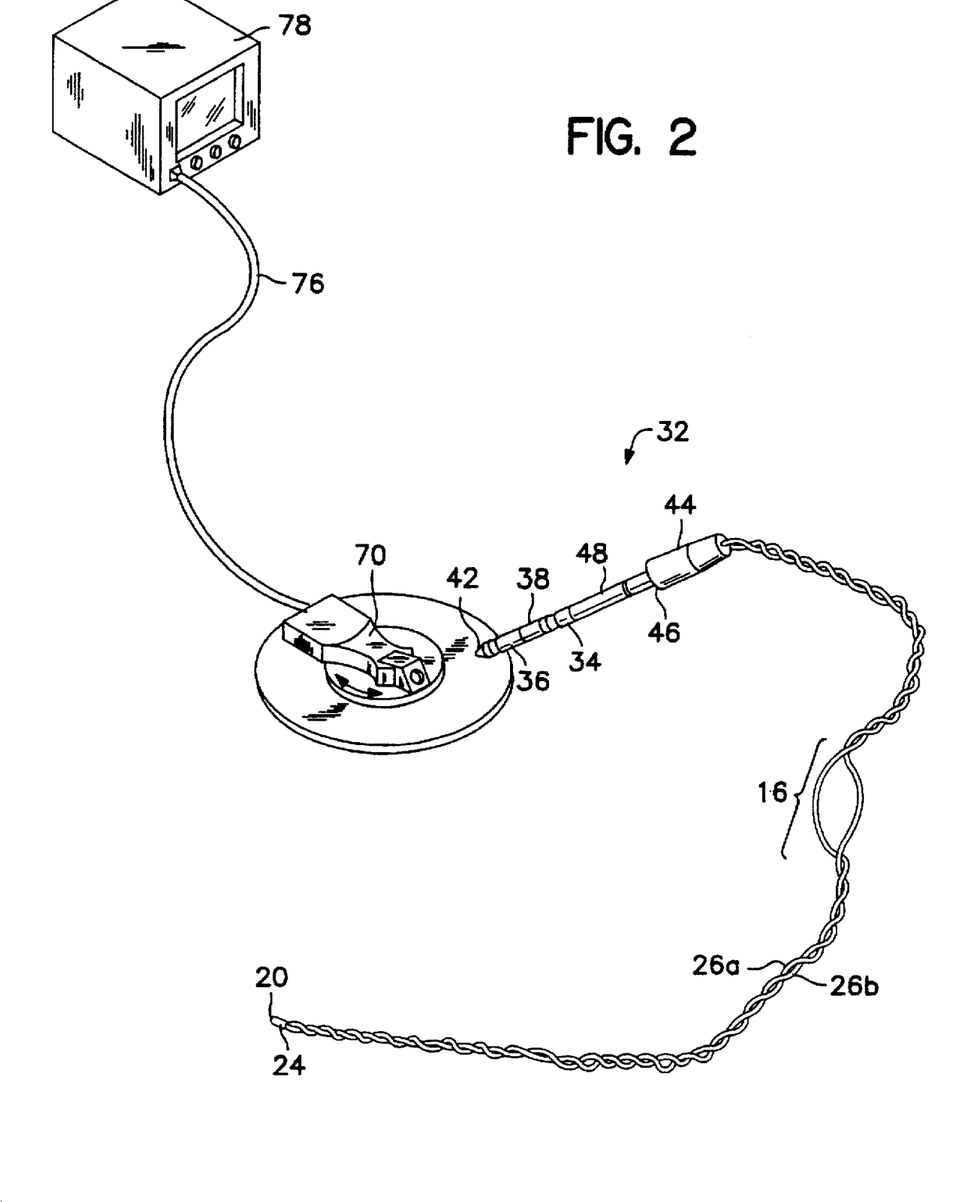
FIG. 2 is a perspective view of the connector of the present invention and illustrates that component in combination with several conventional elements.

Turning to FIG. 2, wires 26a and 26b are provided with an untwisted length 16 along a short distance (25–50 mm or 1–2 inches) of wire strand 18. Untwisted length 16 allows the clinician to separate wires 26a and 26b without cutting them. The individual wires 26a and 26b are separately connected to first and second terminal (or ring) contacts 34 and 36 in connector 32. Contacts 34 and 36 are electrically and physically separated by a spacer 38.

Connector 32 is designed to be inserted into a support plate 70 which is affixed to the mother (typically to the thigh). Support plate 70 is connected, via a cable 76, to a monitor 78. Connector 32 has a forward tapered tip 42 which plugs into a longitudinal passage in the end of handle 50 (connector 32 is shown plugged into the passage in FIG. 1). Moreover, tip 42 of connector 32 abuts a wall in support plate 70 to prevent over-insertion of connector 32. Insertion of connector 32 in support plate 70 connects electrodes 20 and 22 to monitor 78.

Connector 32 has a grip 44 with a diameter sufficiently large (specifically, larger than the outer diameter of introducer 40) and an ergonomically designed shape to permit the user to grasp it easily and to insure a proper, sealed connection of connector 32 to support plate 70. Larger diameter grip 44 of connector 32 renders connector 32 easy to handle, especially with gloved hands. Moreover, the diameter of connector 32 changes, at a shoulder 46 to smaller diameter plug 48 to larger diameter grip 44. The length of smaller diameter plug 48 is selected to correspond to the length by which connector 32 must be inserted fully into support plate 70 to assure optimal signal quality. Thus, connector 32 permits a visual indication of full attachment of connector 32 to support plate 70.

1. The Drive Rod

FIGS. 3 through 8 highlight integral, flexible drive rod 30. Drive rod 30 is slidably received in slotted introducer 40 as shown in FIG. 1. Drive rod 30 transmits torque between handle 50 and clutch 28. The variable shaft flexibility provided by the various regions of drive rod 30 enhances both the ability of the user to push, pull, and rotate the drive rod and the "feel" of the drive rod relative to conventional devices containing shafts of uniform rigidity throughout. The various regions of drive rod 30 are designed to control the torque versus angular deflection characteristics of drive rod 30.

Figure 3:
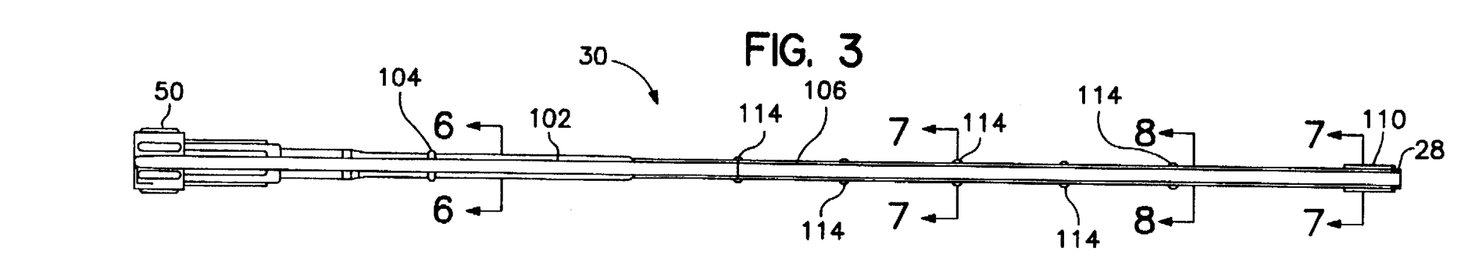
FIG. 3 is a side view of a first embodiment of the drive rod of the present invention.
Figure 4:
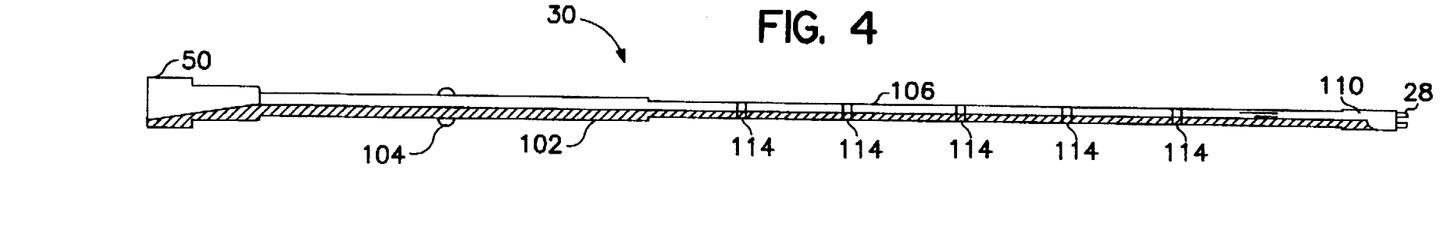
FIG. 4 is a cross-sectional view of the drive rod shown in FIG. 3 illustrating the three regions of varying diameter of the drive rod.
Figure 5:
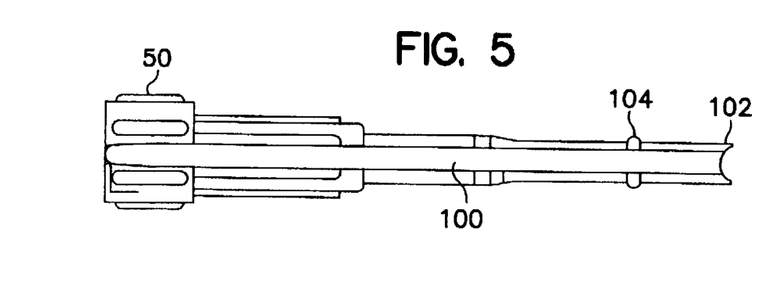
FIG. 5 is an enlarged view of the drive rod shown in FIGS. 3 and 4 highlighting the region of the drive rod adjacent the handle.
Figure 6:
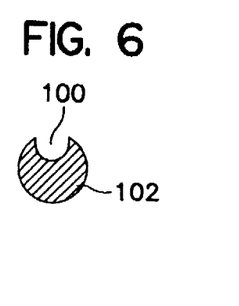
FIG. 6 is a cross-sectional view taken along the line 6—6 of FIG. 3.
Figure 7:
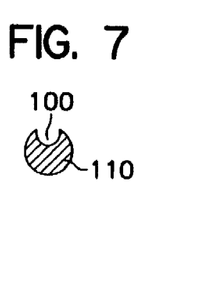
FIG. 7 is a cross-sectional view taken along the lines 7—7 of FIG. 3.
Figure 8:
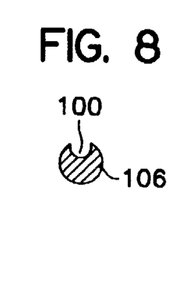
FIG. 8 is a cross-sectional view taken along the line 8—8 of FIG. 3.

Drive rod 30 has three, separate regions along its length to accommodate the variously curved shape of introducer 40. Specifically, the first region 102 adjacent and integral with handle 50, where the minimum drive rod bending exists because introducer 40 is relatively straight in this area, has an outer diameter (about 5.5 mm or 0.22 inches) only slightly less than the inner diameter of introducer 40. The second, central region 106, where the drive rod bending is maximum, typically has a smaller outer diameter (about 4 mm or 0.16 inches) rendering drive rod 30 more flexible. Central region 106 is about 165 mm (6.5 inches) long. Finally, a short region 110 adjacent clutch 28 is provided with an intermediate outer diameter (about 5 mm or 0.20 inches) which is about 12.5 mm (0.5 inches) long.

Drive rod 30 has a channel 100 which runs longitudinally along its entire length. Channel 100 is sized, having a radius of about 0.05 inches (1.2 mm) and a top opening of about 2.4 mm (0.10 inches), to permit wire strand 18 to exit drive rod 30 through channel 100 when drive rod 30 is removed from introducer 40. Wire strand 18 has an outer diameter of about 2 mm (0.08 inches). Thus, wire strand 18 slips out of channel 100 without the need for radial expansion of drive rod 30. The depth of channel 100 is sufficient, however, to prevent wires 26a and 26b from exiting channel 100 and binding on the inner diameter of introducer 40 when drive rod 30 is inside introducer 40.

Central region 106 of drive rod 30 has a number of journals 114 spaced, at intervals of about 1 inch (25 mm), along its length. Journals 114 have a length of about 0.04 inches (1 mm) and an outer diameter approximately equal to the diameter of short region 110 (about 5 mm or 0.20 inches). Thus, the diameter of journals 114 is larger than the diameter of central region 106.

Journals 114 have a height sufficient so that wire strand 18, when placed in channel 100, is tangent to the outer diameter of journals 114. The geometrical relationship between journals 114 and the depth of channel 100 provides a simulated cylinder for uniform contact between wires 26a and 26b and the inside wall of introducer 40. Consequently, smooth, low-friction rotation of drive rod 30 in introducer 40 is assured regardless of the bend angle assumed by introducer 40. This is especially important in central region 106 of drive rod 30 where bend of introducer 40 and drive rod 30 is most pronounced.

Journals 114 each have a notch which corresponds to the width of top opening of channel 100. Removal of drive rod 30 must be accomplished without tugging on wire strand 18. Therefore, the ends of the notches in journals 114 are provided with a radius or chamfer to eliminate sharp edges which might catch wires 26a and 26b as they exit channel 100 of drive rod 30. Untwisted length 16 of wire strand 18 should not be provided along the length of wire strand 18 which must exit channel 100 of drive rod 30; wire strand 18 will exit channel 100 more easily than an untwisted pair of individual wires.

Located on drive rod 30 is an integral safety ring 104 for engaging a series of chambers located within the slotted introducer 40 discussed below. Safety ring 104 is disposed around the entire circumference of drive rod 30 except in the area of channel 100, forming a "C" shape. Typically, safety ring 104 is located approximately 1.25 inches (32 mm) from handle 50 or 2.4 inches (61 mm) from the end of drive rod 30. Safety ring 104 is about 0.12 inches (3 mm) long and has an outer diameter of about 0.25 inches (6.35 mm). Safety ring 104 can be manufactured during the injection molding process typically used to produce drive rod 30. Injection molding offers the advantage of improved dimensional control over the extrusion process.

2. The Slotted Introducer

Figure 9:
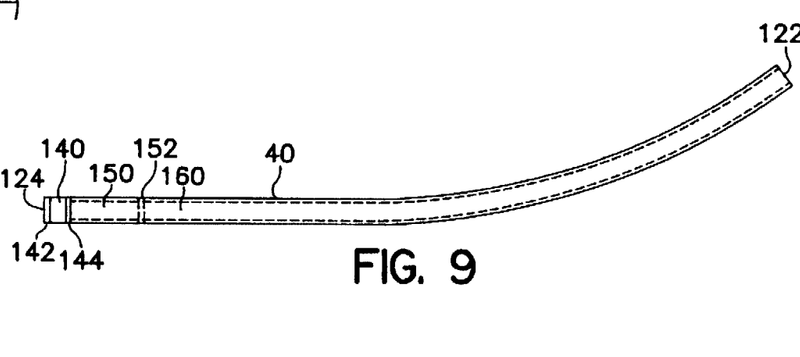
FIG. 9 is a side view of the slotted introducer according to the present invention.

FIGS. 9 through 13 illustrate a first embodiment of introducer 40. Introducer 40 is a curved, form-sustaining member of adjustable shape for insertion of fetal spiral electrode 20 through the mother's cervix and into contact with the fetus during labor. As shown disposed along longitudinal axis "a" in FIG. 10, introducer 40 has a length of about 10.6 inches (270 mm) and a substantially uniform outer diameter of about 0.3 inches (8 mm). Introducer 40 may be shaped, as shown in FIG. 9, with a gentle curve to conform comfortably with the shape of the vagina and cervix of a woman in labor. Introducer 40 can be injection molded, to control the geometry of its inner surface, and formed from a polyolefin (preferably from high-density polyethylene). Any thermoplastic material which is flexible, form-sustaining, and compatible with insertion into the body is suitable for introducer 40.

Figure 10:
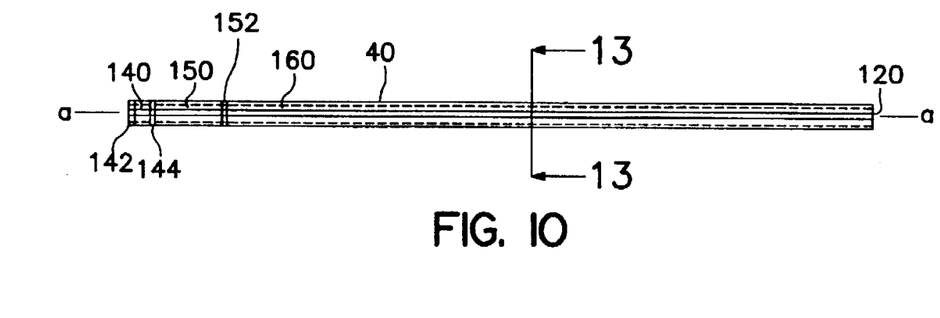
FIG. 10 is a top view showing the longitudinal slot of the introducer of FIG. 9.

Introducer 40 has a longitudinal slot 120, an open front end 122, and an open rear end 124. Slot 120 is placed in the bottom of introducer 40. Such a design is consistent with the '957 patent. Distinguish slotted introducer 40 from a guide tube having a slit. Longitudinal slot 120 is sufficiently wide to permit easy removal of wires 26a and 26b from introducer 40 once fetal spiral electrode 20 has been placed. A "slit" guide tube does not have any space in the resting position; the slit guide tube forms a completed, closed tube in the resting position. In contrast, slotted introducer 40 has a space—slot 120—forming a "C"-shape, in the resting position (see FIG. 13).

Slot 120 is about 0.1 inches (2.5 mm) wide. The width of slot 120 in introducer 40 is wider than the diameter of wire strand 18 to enable easy removal of wire strand 18 from slot 120. Because introducer 40 has longitudinal slot 120 disposed along its entire length, introducer 40 can be removed and discarded once fetal spiral electrode 20 is engaged with the presenting part of the fetus.

Figure 11:
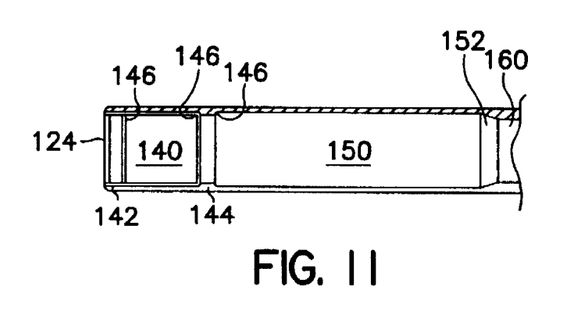
FIG. 11 is a magnified view of the three chambers defined by the inner surface of the slotted introducer shown in FIG. 9.
Figure 12:
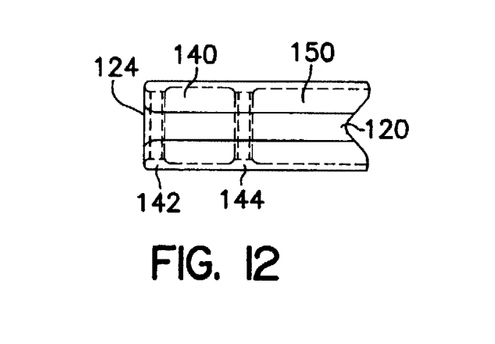
FIG. 12 is a magnified view of the first chamber of the inner surface of the slotted introducer shown in FIG. 10.
Figure 13:
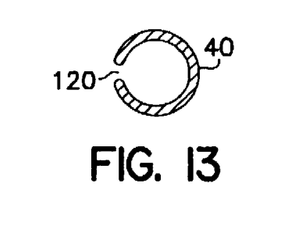
FIG. 13 is a cross-sectional view taken along the line 13—13 of FIG. 10.

According to one embodiment of the present invention, slotted introducer 40 has a first chamber 140 on the inner surface of introducer 40 formed by a rearward interior wall 142 and a forward interior wall 144. First chamber 140 is located adjacent rear end 124 of introducer 40. Interior walls 142 and 144 are "C"-shaped rings having chamfers 146 angled at 45 degrees. The width of rearward interior wall 142 is about 0.06 inches (1.5 mm) and the width of forward interior wall 144 is about 0.04 inches (1 mm). The width of first chamber 140, from rear end 124 of introducer 40 to the center of forward interior wall 144, is about 0.345 inches (8.8 mm). Alternatively, the width of first chamber 140 could be made only slightly larger than the width of safety ring 104 to reduce the "play" of safety ring 104 when positioned in first chamber 140.

The inner diameter of first chamber 140 is about 0.26 inches (6.6 mm). Interior walls 142 and 144 disposed on the inner surface of introducer 140 each have an inner diameter of about 0.238 inches (6.0 mm). As stated above, safety ring 104 has an outer diameter of about 0.25 inches (6.35 mm). Thus, interior walls 142 and 144 provide constricted regions having inner diameters which are smaller than the outer diameter of safety ring 104 located on the outer surface of drive rod 30. The inner diameter of first chamber 140 is large enough so that no outward radial stresses are exerted upon introducer 40 by safety ring 104 when safety ring 104 is located in chamber 140. Accordingly, relaxation of the inside wall of slotted introducer 40 is prevented during storage of electrode system 10.

Upon insertion of drive rod 30 into rear end 124 of introducer 40, safety ring 30 passes rearward interior wall 142 and enters first chamber 140 where it is prevented from moving forward by forward interior wall 144. Electrode system 10 is stored in this position. The coordinated locations of first chamber 140 and safety ring 104 on introducer 40 and drive rod 30, respectively, maintain drive rod 30 in a predetermined position such that fetal spiral electrode 20 and holder 24 engaged in clutch 28 are retracted inside slotted introducer 40. In this manner, fetal spiral electrode 20 is protected inside introducer 40 until slotted introducer 40 contacts the presenting part of the fetus to which fetal spiral electrode 20 will be attached.

The combination of safety ring 104 and first chamber 140 helps to prevent harm or injury to the fetus and maternal tissue and contamination of fetal spiral electrode 20 by preventing fetal spiral electrode 20 from moving forward until an intentional forward force is applied to drive rod handle 50. The forward force to be applied must be sufficient for safety ring 104 to expand forward interior wall 144, thereby permitting drive rod 30 to move forward such that fetal spiral electrode 20 is exposed. Expansion of forward interior wall 144 is possible because introducer 40 has slot 120. The geometry of safety ring 104 and forward interior wall 144, as well as the materials of construction for those components, can be selected to pre-determine the force required to expose fetal spiral electrode 20. Fetal spiral electrode 20 is then attached to the fetal epidermis by rotating handle 50 of drive rod 30.

Once safety ring 104 expands beyond forward interior wall 144, it enters second chamber 150. The inner diameter of second chamber 150 is identical to the inner diameter of first chamber 140, namely about 0.26 inches (6.6 mm). Second chamber 150 ends at a throat 152 at which the inner diameter of introducer 40 tapers from an inner diameter in second chamber 150 of about 0.26 inches (6.6 mm) to an inner diameter of about 0.238 inches (6.0 mm) in third chamber 160. Second chamber 150 extends from forward interior wall 144 to throat 152, a distance of about 1 inch (25.4 mm). Third chamber 160 extends from throat 152 to front end 122 of introducer 40.

The walls of introducer 40 defining first chamber 140 and second chamber 150 are about 0.025 inches (0.64 mm) thick. The walls of introducer 40 defining third chamber 160 have a thickness identical to interior walls 142 and 144 defining first chamber 140, namely 0.036 inches (0.9 mm). Throat 152 tapers at an angle of about ten degrees between second chamber 150 and third chamber 160.

As discussed above, clutch 28 on the end of drive rod 30 engages reference electrode 22 on holder 24. The engagement is loose, not fixed, and depends on continued axial alignment between holder 24 and clutch 28. Such alignment is assured as long as holder 24 and drive rod 30 are both restrained in introducer 40. Once holder 24 exits front end 122 of introducer 40, however, holder 24 may fall away from drive rod 30. If so, clutch 28 and reference electrode 22 will no longer be aligned axially and may disengage. Therefore, it is important that drive rod 30 not be pushed toward front end 122 of introducer 40 so far as to cause holder 24 to exit front end 122 of introducer 40.

Throat 152 minimizes the risk that holder 24 will exit front end 122 of introducer 40. As drive rod 30 is pushed toward front end 122, with safety ring 104 in second chamber 150, safety ring 104 approaches throat 152. Safety ring 152 gradually restricts forward movement of drive rod 30 as safety ring 104 engages the tapered wall of throat 152. Continued forward movement of drive rod 30 is difficult if safety ring 104 passes throat 152 and enters third chamber 160. When the user feels the restriction on forward movement of drive rod 30, it becomes clear that fetal spiral electrode 20 has not contacted tissue and a risk arises that continued forward movement of drive rod 30 will cause holder 24 to exit front end 122 of introducer 40. This cautions the user to retract drive rod 30 (and, in turn, holder 24 and fetal spiral electrode 20) and to reposition electrode system 10. The length of second chamber 150 is selected to correspond to the distance that drive rod 30 may travel forward in introducer 40 before holder 24 exits front end 122 of introducer 40.

Electrode system 10 is stored with safety ring 104 retained between rearward interior wall 142 and forward interior wall 144 in first chamber 140. Preferably, first chamber 140 has an inner diameter large enough so that no outward radial stresses are exerted upon introducer 40 by safety ring 104 when it is located in first chamber 140. Given an outer diameter for safety ring 104 of about 0.25 inches (6.35 mm), first chamber 140 may have an inner diameter of about 0.26 inches (6.6 mm). These dimensions prevent relaxation of the inside wall of slotted introducer 40 during storage of electrode system 10.

To use electrode system 10 of the present invention, slotted introducer 40 is inserted through the mother's cervix and into contact with the fetus with safety ring 104 of drive rod 30 still located in first chamber 140 of introducer 40. Fetal spiral electrode 20 is in its retracted position within introducer 40. Drive rod 30 is pushed by applying a forward force to handle 50 sufficient to move safety ring 104 out of first chamber 140 of slotted introducer 40. (There is no need to pull back on drive rod 30 to release a safety tab as for certain known devices.) Drive rod 30 is then advanced until fetal spiral electrode 20 contacts the fetus. While pressure is maintained against the fetus with both introducer 40 and drive rod 30, drive rod 30 is rotated until fetal spiral electrode 20 is secured to the fetal epidermis. Typically, one full revolution suffices to secure fetal spiral electrode 20.

Slotted introducer 40 and drive rod 30 are then removed, either sequentially, with drive rod 30 being removed first, or simultaneously, to leave fetal spiral electrode 20, reference electrode 22, holder 24, and wires 26a and 26b inside the mother. Wires 26a and 26b slip out of channel 100 of drive rod 30; drive rod 30 essentially slides away from wires 26a and 26b. Similarly, wires 26a and 26b slip out of slot 120 of introducer 40; introducer 40 essentially slides away from wires 26a and 26b. Thus, the size of connector 52 on the end of wires 26a and 26b is not confined to any diameter of introducer 40 or drive rod 30. Once introducer 40 and drive rod 30 are removed, connector 52 is attached to support plate 70 for monitoring the fetal heart rate.

Figure 14:
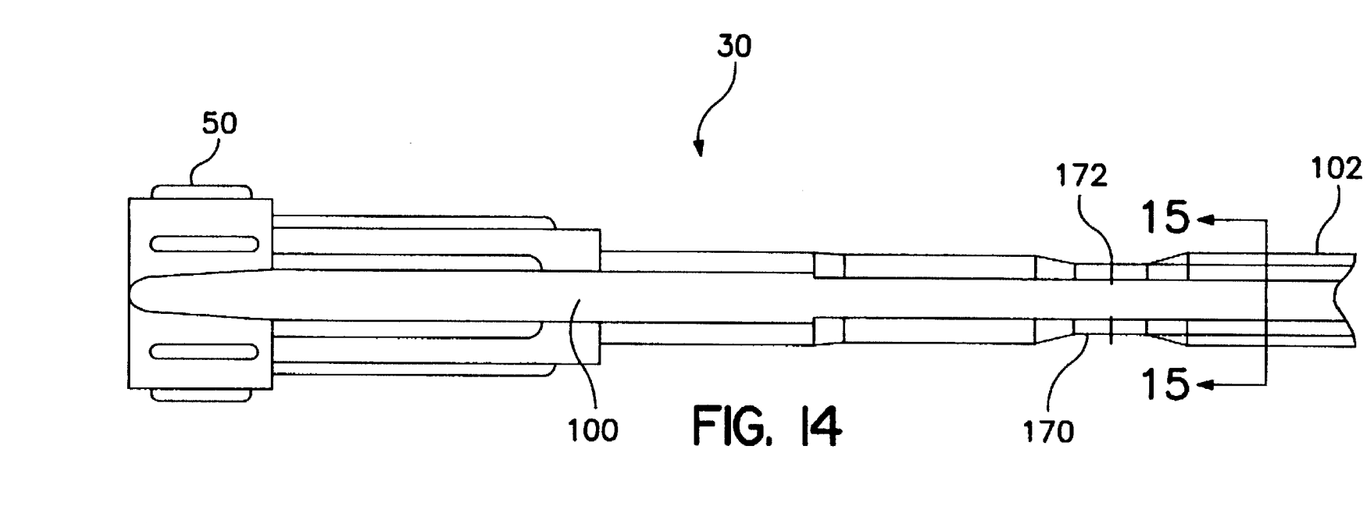
FIG. 14 is a top view of the rearward end of the second embodiment of the drive rod of the present invention, illustrating the radial web.
Figure 15:
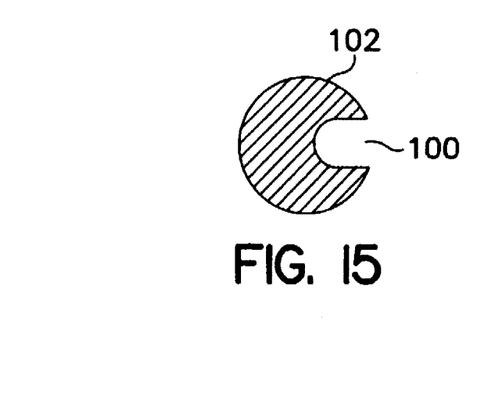
FIG. 15 is a cross-sectional view taken along the line 15—15 of FIG. 14.

In an alternative embodiment according to the present invention, FIGS. 14 and 15 illustrate drive rod 30 having a recessed portion 170 and a radial web 172. Drive rod 30 can be used with a conventional introducer having a constant inner diameter (not shown). Preferably, the conventional introducer is slotted (see the '957 patent) to facilitate both expansion of the introducer and removal of electrode wires 26a and 26b as described above. The outer diameter of radial web 172 is slightly greater than the inner diameter of the introducer; therefore, a friction fit is established between the introducer and radial web 172. The friction fit maintains drive rod 30 in a predetermined position within the introducer, such that fetal spiral electrode 20 remains in a retracted position within the introducer, until the user intentionally advances drive rod 30 against the frictional resistance.

As drive rod 30 is pushed forward in the introducer, radial web 172 contacts the inside surface of the introducer. Radial web 172 is sufficiently flexible, however, that it can be pushed through the introducer if a predetermined force is applied to handle 50 of drive rod 30. If a slotted introducer is used, less force will be required because the introducer will expand as radial web 172 traverses through the introducer.

Typically, radial web 172 is manufactured during an injection molding process used to produce drive rod 30. This is accomplished by providing a slight split in the cavity blocks used to mold drive rod 30 such that a void having the desired dimensions of radial web 172 occurs at the desired location along the length of drive rod 30. During the injection molding process, the pressure with which the molding material is introduced forces material into the void and forms radial web 172. The dimensions of radial web 172 can be varied by adjusting the size of the void used during the injection molding process.

Typically, when using a polypropylene or polyethylene molding material to produce drive rod 30, radial web 172 having a thickness of between 0.006–0.010 inches (0.15–0.25 mm) is provided to give the flexibility required to produce a friction fit when placed inside an introducer. The outer diameter of radial web 172 is slightly greater than the inner diameter of the introducer to ensure the proper friction fit.

The second embodiment of drive rod 30 having radial web 172 is used to apply fetal spiral electrode 20 in much the same manner as the first embodiment having safety ring 104. The major difference between the method of using these embodiments is that it is the friction fit of radial web 172 against the inner surface of the introducer, rather than abutment of safety ring 104 with forward interior wall 144 of introducer 40, which is relied upon to retain drive rod 30 and fetal spiral electrode 20 in a retracted position until intentionally advanced by the user.

The second embodiment of drive rod 30 having radial web 172 may also be used in conjunction with introducer 40 having first chamber 140 on the inner surface of introducer 40 formed by a rearward interior wall 142 and a forward interior wall 144—as described above. Radial web 172 simply replaces safety ring 104 on drive rod 30 and has an outer diameter of at least 0.25 inches (6.35 mm). Thus, interior walls 142 and 144 provide constricted regions having inner diameters which are smaller than the outer diameter of radial web 172 located on the outer surface of drive rod 30. The inner diameter of first chamber 140 is large enough so that no outward radial stresses are exerted upon introducer 40 by radial web 172 when radial web 172 is located in chamber 140.

When radial web 172 simply replaces safety ring 104 on drive rod 30, the second embodiment of drive rod 30 having radial web 172 is used to apply fetal spiral electrode 20 in the same manner as the first embodiment having safety ring 104. Radial web 172 abuts forward interior wall 144 of introducer 40 to retain drive rod 30 and fetal spiral electrode 20 in a retracted position until intentionally advanced by the user. Upon application of a predetermined forward force to drive rod 30, flexible radial web 172 passes forward interior wall 144 and permits drive rod 30 to move forward such that fetal spiral electrode 20 is exposed. Introducer 40 may have a slot 120 enabling forward interior wall 144 to expand as radial web 172 passes. Alternatively, a closed introducer (without slot 120) may be used, relying entirely on the flexibility of radial web 172 to allow radial web 172 to pass forward interior wall 144.

Figure 16:
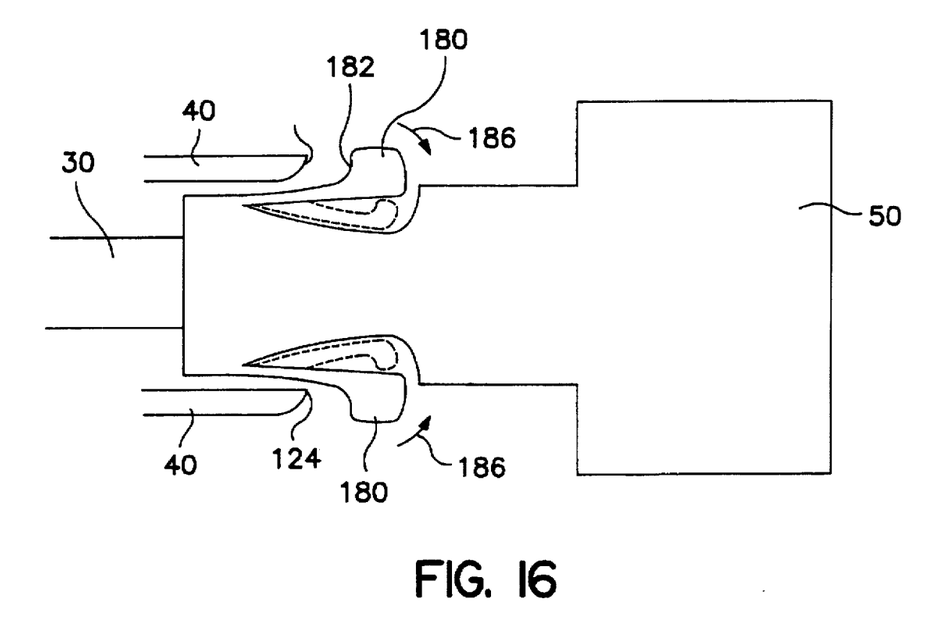
FIG. 16 is a top view of the rearward end of the third embodiment of the drive rod of the present invention, illustrating the segmented rib.

FIG. 16 illustrates the rearward end of the third embodiment of drive rod 30 of the present invention. Handle 50 of drive rod 30 is provided with a segmented rib 180. To facilitate manufacture, segmented rib 180 may be formed of two, separate segments which, when taken together, combine to cover substantially the entire circumference of drive rod 30 except the area of channel 100. Segmented rib 180 contacts rear end 124 of introducer 40 and resists insertion of drive rod 30 into introducer 40. Consequently, fetal spiral electrode 20 is retained within introducer 40.

When the user desires to apply fetal spiral electrode 20 to the fetal epidermis, a predetermined axial force is applied to handle 50. This force allows curve 182 on segmented rib 180 to slide past ramp 184 on rear end 124 of introducer 40. Segmented rib 180 then assumes the position shown by the dashed lines in FIG. 16, having moved in the direction of arrows 186. Segmented rib 180 will continue to resist, but allow, axial movement of drive rod 30 through introducer 40 in a manner similar to the frictional resistance between the introducer and radial web 172 described above.

Also like the second embodiment of drive rod 30 having radial web 172 described above, segmented rib 180 may be used in conjunction with introducer 40 having first chamber 140 on the inner surface of introducer 40 formed by a rearward interior wall 142 and a forward interior wall 144. Segmented rib 180 simply replaces safety ring 104 (or radial web 172) on drive rod 30 and has an outer diameter of at least 0.25 inches (6.35 mm). Thus, interior walls 142 and 144 provide constricted regions having inner diameters which are smaller than the outer diameter of segmented rib 180 located on the outer surface of drive rod 30.

When segmented rib 180 simply replaces safety ring 104 or radial web 172 on drive rod 30, the third embodiment of drive rod 30 having segmented rib 180 is used to apply fetal spiral electrode 20 in the same manner as the first embodiment having safety ring 104 and the second embodiment having radial web 172. Segmented rib 180 abuts forward interior wall 144 of introducer 40 to retain drive rod 30 and fetal spiral electrode 20 in a retracted position until intentionally advanced by the user. Upon application of a predetermined forward force to drive rod 30, segmented rib 180 passes forward interior wall 144 and permits drive rod 30 to move forward such that fetal spiral electrode 20 is exposed. Introducer 40 may have a slot 120 enabling forward interior wall 144 to expand as segmented rib 180 passes.

The introducer and drive rod system of the present invention is integrated in that it is used with the components (e.g., fetal spiral electrode 20, holder 24, connecting wires 26a and 26b, and connector 32) of conventional electrode systems. Because no separate, added components are involved, the system is integral with existing components. The system is easy to use; it only requires one hand to manipulate and can be operated without regard to directionality. The configuration of the slotted introducer also permits production methods, such as injection molding, which offer advantages over the extrusion methods used to produce prior art guide tubes. As a result, the geometry of the inner surface of the slotted introducer can be better controlled.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention. The integrated introducer and drive rod system in accordance with the present invention can be used, for example, to attach spiral-shaped, biological needle probes other than the fetal spiral electrode shown in the '990 patent. Because a fetal spiral electrode is the preferred version of the probe, however, the system is illustrated incorporating such an electrode.

What is claimed is:

1. An integrated introducer and drive rod system used to position and attach a probe to a fetus during labor and delivery, said system comprising:

a drive rod having:
 (a) a circumference with an outside diameter,
 (b) a forward end,
 (c) a rearward end,
 (d) a handle on said rearward end imparting translation and rotation to said drive rod, and
 (e) means disposed around the circumference of said drive rod for resisting and, upon exertion of a predetermined force on said handle, allowing translation of said drive rod; and an introducer having:
 (a) an open front end,
 (b) an open rear end,
 (c) an outer diameter only slightly greater than the outside diameter of said drive rod,
 (d) an inner diameter,
 (e) means disposed around the inner diameter of said introducer for resisting and, upon exertion of said predetermined force on said handle of said drive rod, allowing translation of said drive rod within said introducer, and
 (f) a length with a longitudinal slot disposed along the entire length.

2. The system according to claim 1 wherein said drive rod means for resisting and allowing translation of said drive rod is a "C"-shaped safety ring around the circumference of said drive rod, said safety ring having an outside diameter.

3. The system according to claim 2 wherein said introducer means for resisting and allowing translation of said drive rod includes a forward interior wall having an inside diameter slightly less than said outside diameter of said safety ring.

4. The system according to claim 3 wherein said introducer means for resisting and allowing translation of said drive rod further includes a rearward interior wall having an inside diameter slightly less than said outside diameter of said safety ring, said rearward interior wall and said forward interior wall defining a chamber retaining said safety ring until said predetermined force is exerted on said handle.

5. The system according to claim 1 wherein said drive rod means for resisting and allowing translation of said drive rod is a "C"-shaped radial web around the circumference of said drive rod, said radial web having an outside diameter only slightly larger than said inner diameter of said introducer creating an interference fit between said drive rod and said introducer.

6. The system according to claim 1 wherein said drive rod means for resisting and allowing translation of said drive rod is a "C"-shaped segmented rib around the circumference of said drive rod, said segmented rib engaging said rear end of said introducer.

7. The system according to claim 6 wherein said introducer means for resisting and allowing translation of said drive rod includes a ramp on said rear end of said introducer.

8. A system used to monitor the fetus of a mother during labor and delivery, said system delivering signals to a monitor external to the mother and comprising:

a probe adapted to be attached to the fetus;
a wire strand including a pair of wires connected to said probe on one end and adapted to be connected to the monitor on the opposite end;
a solid drive rod having:
 (a) a circumference with an outside diameter,
 (b) a forward end,
 (c) a rearward end,
 (d) a handle on said rearward end imparting translation and rotation to said drive rod,
 (e) a clutch on said forward end imparting translation and rotation to said probe to secure attachment of said probe to the fetus,
 (f) a channel longitudinally disposed in said drive rod and transporting said twisted wire strand from said probe to the monitor, and
 (g) a "C"-shaped safety ring having an outside diameter and being disposed around the circumference of said drive rod, except in the area of said channel, said safety ring resisting and, upon exertion of a predetermined force on said handle, allowing translation of said drive rod; and an introducer having:
 (a) an open front end,
 (b) an open rear end,
 (c) an outer diameter only slightly greater than the outside diameter of said drive rod and adapted to be comfortably inserted through the cervix of the mother,
 (d) an inner diameter, and
 (e) a forward interior wall being disposed around the inner diameter of said introducer and having an inside diameter slightly less than said outside diameter of said safety ring, said forward interior wall resisting and, upon exertion of said predetermined force on said handle of said drive rod, allowing translation of said drive rod within said introducer.

9. The system according to claim 8 wherein said safety ring is positioned on said drive rod about 30 mm from said handle.

10. The system according to claim 9 wherein said outside diameter of said safety ring is about 6 mm.

11. The system according to claim 8 wherein said introducer has a rearward interior wall disposed around said inner diameter of said introducer adjacent said rear end of said introducer, said rearward interior wall having an inside diameter slightly less than said outside diameter of said safety ring, said rearward interior wall and said forward interior wall defining a first chamber retaining said safety ring until said predetermined force is exerted on said handle.

12. The system according to claim 11 wherein said forward interior wall is positioned on said introducer about 9 mm from said rear end of said introducer.

13. The system according to claim 11 wherein said first chamber has an inner diameter slightly greater than said outside diameter of said safety ring.

14. The system according to claim 13 wherein said introducer has a throat disposed around said inner diameter of said introducer, said throat and said forward interior wall defining a second chamber having an inner diameter slightly greater than said outside diameter of said safety ring, said throat and said front end of said introducer defining a third chamber having an inner diameter slightly less than said outside diameter of said safety ring, said throat tapering from said second chamber to said third chamber.

15. The system according to claim 14 wherein said taper of said throat is about ten degrees.

16. The system according to claim 14 wherein said second chamber is about 25 mm long.

17. The system according to claim 8 wherein said introducer has a longitudinal slot disposed along its entire length, said slot having a width sufficient to permit passage of the twisted wire strand and expansion of said forward interior wall upon exertion of said predetermined force on said handle of said drive rod, thereby allowing translation of said drive rod.

18. The system according to claim 17 wherein said slot of said introducer is about 2.5 mm wide.

19. A system used to monitor the fetus of a mother during labor and delivery, said system delivering signals to a monitor external to the mother and comprising:

a probe adapted to be attached to the fetus;

a wire strand including a pair of wires connected to said probe on one end and adapted to be connected to the monitor on the opposite end;

a solid drive rod having:
  (a) a circumference with an outside diameter,
  (b) a forward end,
  (c) a rearward end,
  (d) a handle on said rearward end imparting translation and rotation to said drive rod,
  (e) a clutch on said forward end imparting translation and rotation to said probe to secure attachment of said probe to the fetus,
  (f) a channel longitudinally disposed in said drive rod and transporting said twisted wire strand from said probe to the monitor, and
  (g) a "C"-shaped safety ring having an outside diameter and being disposed around the circumference of said drive rod, except in the area of said channel, said safety ring resisting and, upon exertion of a predetermined force on said handle, allowing translation of said drive rod; and an introducer having:
  (a) an open front end,
  (b) an open rear end,
  (c) an outer diameter only slightly greater than the outside diameter of said drive rod and adapted to be comfortably inserted through the cervix of the mother,
  (d) an inner diameter;
  (e) a forward interior wall being disposed around the inner diameter of said introducer and having an inside diameter slightly less than said outside diameter of said safety ring, said forward interior wall resisting and, upon exertion of said predetermined force on said handle of said drive rod, allowing translation of said drive rod within said introducer;
  (f) a rearward interior wall disposed around said inner diameter of said introducer adjacent said rear end of said introducer, said rearward interior wall having an inside diameter slightly less than said outside diameter of said safety ring, said rearward interior wall and said forward interior wall defining a first chamber retaining said safety ring until said predetermined force is exerted on said handle and having an inner diameter slightly greater than said outside diameter of said safety ring;
  (g) a throat disposed around said inner diameter of said introducer, said throat and said forward interior wall defining a second chamber having an inner diameter slightly greater than said outside diameter of said safety ring, said throat and said front end of said introducer defining a third chamber having an inner diameter slightly less than said outside diameter of said safety ring, said throat tapering from said second chamber to said third chamber; and
  (h) a longitudinal slot disposed along the entire length of said introducer, said slot having a width sufficient to permit passage of the twisted wire strand and expansion of said forward interior wall upon exertion of said predetermined force on said handle of said drive rod, thereby allowing translation of said drive rod within said introducer.

20. A system used to monitor the fetus of a mother during labor and delivery, said system delivering signals to a monitor external to the mother and comprising:

a probe adapted to be attached to the fetus;

a wire strand including a pair of wires connected to said probe on one end and adapted to be connected to the monitor on the opposite end;

a solid drive rod having:
  (a) a circumference with an outside diameter,
  (b) a forward end,
  (c) a rearward end,
  (d) a handle on said rearward end imparting translation and rotation to said drive rod,
  (e) a clutch on said forward end imparting translation and rotation to said probe to secure attachment of said probe to the fetus,
  (f) a channel longitudinally disposed in said drive rod and transporting said twisted wire strand from said probe to the monitor, and
  (g) a flexible, "C"-shaped radial web with an outside diameter disposed around the circumference of said drive rod except in the area of said channel, said radial web resisting and, upon exertion of a predetermined force on said handle, allowing translation of said drive rod; and an introducer having:
(a) an open front end,
(b) an open rear end,
(c) an outer diameter only slightly greater than the outside diameter of said drive rod and adapted to be comfortably inserted through the cervix of the mother, and
(d) an inner diameter slightly smaller than said outside diameter of said radial web, said inner diameter of said introducer and said outside diameter of said radial web of said drive rod creating an interference fit between said drive rod and said introducer resisting and, upon exertion of a predetermined force on said handle of said drive rod, allowing translation of said drive rod within said introducer.

21. The system according to claim 20 wherein said radial web has a thickness of between 0.15 and 0.25 mm.

22. The system according to claim 20 wherein said introducer has a longitudinal slot disposed along the entire length of said introducer, said slot having a width sufficient to permit passage of the twisted wire strand and expansion of said inner diameter upon exertion of said predetermined force on said handle of said drive rod, thereby allowing translation of said drive rod within said introducer.

23. A system used to monitor the fetus of a mother during labor and delivery, said system delivering signals to a monitor external to the mother and comprising:

a probe adapted to be attached to the fetus;

a wire strand including a pair of wires connected to said probe on one end and adapted to be connected to the monitor on the opposite end;

a solid drive rod having:
(a) a circumference with an outside diameter,
(b) a forward end,
(c) a rearward end,
(d) a handle on said rearward end imparting translation and rotation to said drive rod,
(e) a clutch on said forward end imparting translation and rotation to said probe to secure attachment of said probe to the fetus,
(f) a channel longitudinally disposed in said drive rod and transporting said twisted wire strand from said probe to the monitor, and
(g) a "C"-shaped segmented rib around the circumference of said drive rod except in the area of said channel, said segmented rib engaging said rear end of said introducer, resisting translation of said drive rod, and, upon exertion of a predetermined force on said handle, allowing translation of said drive rod;

an introducer having:
(a) an open front end,
(b) an open rear end with a ramp resisting and, upon exertion of said predetermined force on said handle of said drive rod, allowing translation of said drive rod within said introducer,
(c) an outer diameter only slightly greater than the outside diameter of said drive rod and adapted to be comfortably inserted through the cervix of the mother, and
(d) an inner diameter.

24. The system according to claim 23 wherein said introducer has a longitudinal slot disposed along the entire length of said introducer, said slot having a width sufficient to permit passage of the twisted wire strand and expansion of said inner diameter upon exertion of said predetermined force on said handle of said drive rod, thereby allowing translation of said drive rod within said introducer.

* * * * *